(12) United States Patent
Hickey

(10) Patent No.: US 12,021,648 B2
(45) Date of Patent: Jun. 25, 2024

(54) DISEASE ALERT SYSTEM

(71) Applicant: Roger William Hickey, Huntington Beach, CA (US)

(72) Inventor: Roger William Hickey, Huntington Beach, CA (US)

( * ) Notice: Subject to any disclaimer, the term of this patent is extended or adjusted under 35 U.S.C. 154(b) by 284 days.

(21) Appl. No.: 17/535,308

(22) Filed: Nov. 24, 2021

(65) Prior Publication Data

US 2023/0163989 A1     May 25, 2023

(51) Int. Cl.
*H04L 12/18*     (2006.01)
*G16H 40/67*     (2018.01)

(52) U.S. Cl.
CPC ......... *H04L 12/1895* (2013.01); *G16H 40/67* (2018.01)

(58) Field of Classification Search
CPC .... H04L 12/1895; G16H 40/67; H04M 11/04; H04M 2242/04
USPC ....................................................... 370/259
See application file for complete search history.

(56) References Cited

U.S. PATENT DOCUMENTS

| | | | | |
|---|---|---|---|---|
| 2011/0158130 A1* | 6/2011 | Liu | ....................... | H04M 15/85 370/352 |
| 2014/0320289 A1* | 10/2014 | Raichman | ............. | G08B 21/245 340/573.1 |
| 2016/0171179 A1* | 6/2016 | Donofrio | ............... | G16H 50/70 705/2 |
| 2016/0179089 A1* | 6/2016 | Stratmann | ............... | E05F 15/70 700/231 |
| 2021/0350689 A1* | 11/2021 | Kelly | .................... | G08B 21/245 |

FOREIGN PATENT DOCUMENTS

| | | | | |
|---|---|---|---|---|
| CN | 111403045 | 6/2016 | | |
| WO | WO2016089914 | 6/2016 | | |
| WO | WO2021201329 | 10/2021 | | |
| WO | WO-2021201329 A1 * | 10/2021 | ........... | A61B 5/0008 |
| WO | WO-2021222166 A1 * | 11/2021 | ......... | A61B 5/02055 |

OTHER PUBLICATIONS

Author: Centers for Disease Control and Prevention; Title: Electronice Disease Notification System; Date: Sep. 26, 2019.

* cited by examiner

*Primary Examiner* — Ahmad F. Matar
*Assistant Examiner* — Jirapon Tulop
(74) *Attorney, Agent, or Firm* — Eric Karich; Karich & Associates

(57) ABSTRACT

A germ alert system sends a public alert to a plurality of user computer devices, and transmits an activation signal to activate a plurality of disinfection devices in response to the detection of a potential epidemic. The system performs the steps of receiving a triggering alert of the potential epidemic, transmitting the public alert via a computer network to the plurality of user computer devices, and transmitting the activation signal to the plurality of disinfection devices.

11 Claims, 3 Drawing Sheets

DISEASE ALERT SYSTEM

BACKGROUND OF THE INVENTION

Field of the Invention

This invention relates generally to germ alert systems, and more particularly to a germ alert system that not only alerts the public in the event of an epidemic, but also automatically activates disinfection devices. The system also provides public instructions as to where it is safer, and what to do in case of a pandemic emergency (e.g., directions to local help, solutions to common problems, a safety network, and the nearest medical facilities handling medical care related to the pandemic and germ outbreaks.

Description of Related Art

The prior art teaches a variety of germ alert systems. For example, the CDC (Centers for Disease Control and Prevention) utilizes an electronic disease notification system that provides a centralized reporting system that notifies US state and local health departments and screening clinics of the arrival of immigrants with health conditions. However, the existing systems do not function to notify the public directly of impending pandemic events. The current invention will function to notify all people involved, from the general public, to schools, shelters, medical facilities, government administrations, people working the travel industry, etc.

Importantly, only authorized health officials can access this system. The system does not provide any warning to the public of potential epidemics. Also, the system does not automatically trigger disease control efforts, such as activating disinfection devices.

The current germ alert system sends a public alert to a plurality of user computer devices (i.e., the public), and transmits an activation signal to activate a plurality of disinfection devices in response to the detection of a potential epidemic. The system also performs the steps of receiving a triggering alert of the potential epidemic, transmitting the public alert via a computer network to the plurality of user computer devices, and transmitting the activation signal to the plurality of disinfection devices.

SUMMARY OF THE INVENTION

The present invention teaches certain benefits in construction and use which give rise to the objectives described below.

The present invention provides a germ alert system sends a public alert to a plurality of user computer devices, and transmits an activation signal to activate a plurality of disinfection devices in response to the detection of a potential epidemic. The system performs the steps of receiving a triggering alert of the potential epidemic and pandemic, transmitting the public alert via a computer network to the plurality of user computer devices, and transmitting the activation signal to the plurality of disinfection devices.

A primary objective of the present invention is to provide a germ alert system having advantages not taught by the prior art.

Another objective is to provide a germ alert system that creates a global alert system directly targeted to germ and disease epidemics and pandemic outbreaks.

Another objective is to provide a germ alert system that enables a public alert to be sent in the case of an epidemic.

A further objective is to provide a germ alert system that activates a plurality of disinfection devices to operate in the case of an epidemic.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate some of the present invention.

DETAILED DESCRIPTION OF THE INVENTION

Figure 1:
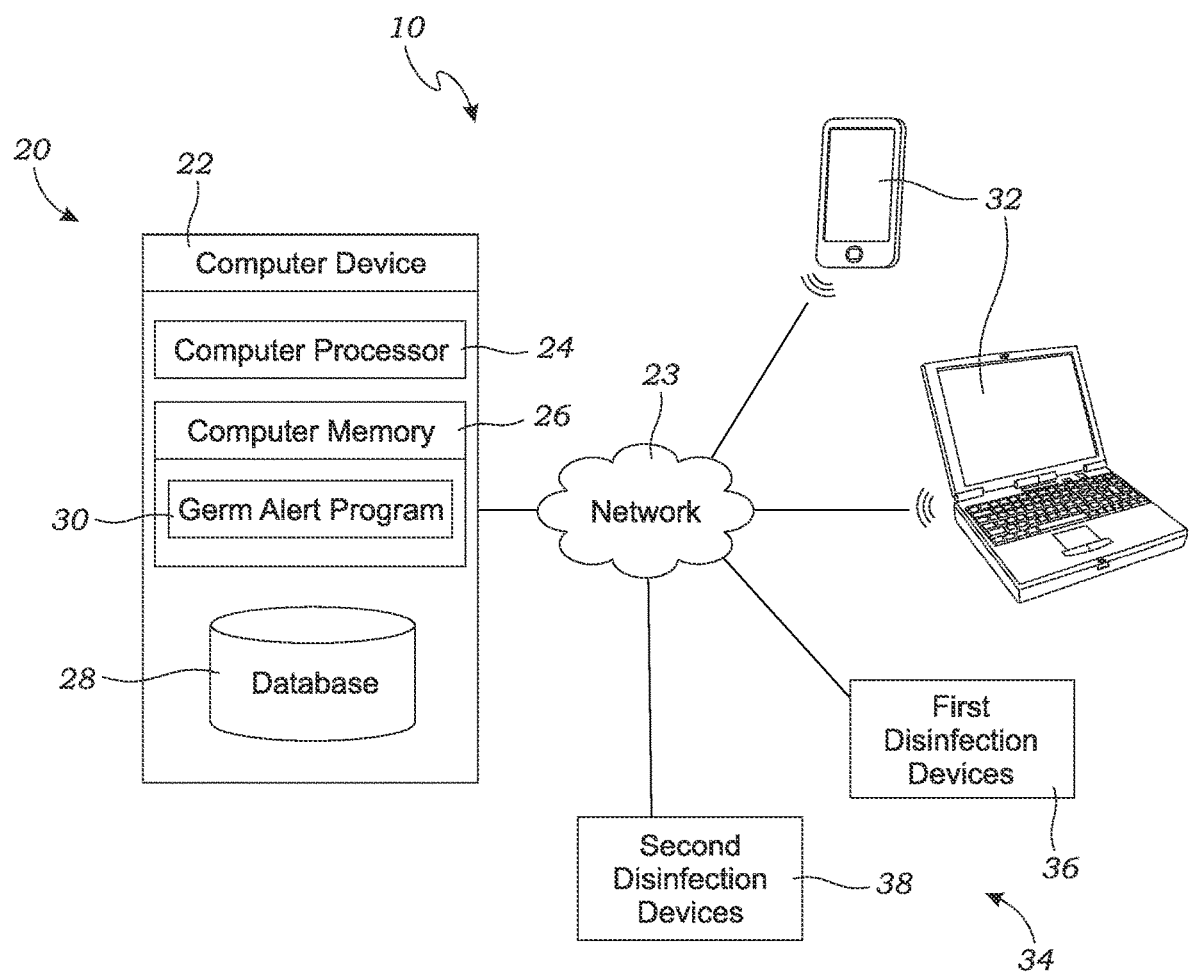
FIG. 1 is a block diagram of one embodiment of a computer system that embodies the present invention.

The above-described drawing figures illustrate the invention, a germ alert system for transmitting a public alert to a plurality of user computer devices, and for transmitting an activation signal to activate a plurality of disinfection devices in response to the detection of a potential epidemic.

The following includes definitions of selected terms employed herein:

The terms "computer," "computer device," and "server" as used herein, refer to a device and/or system of devices that include at least one computer processing element, e.g., a central processing unit (CPU), and some form of computer memory having a capability to store data. The computer may comprise hardware, software, and firmware for receiving, storing, and/or processing data as described below. For example, a computer may comprise any of a wide range of digital electronic devices, including, but not limited to, a server, a desktop computer, a laptop, a smart phone, a tablet, or any form of electronic device capable of functioning as described herein.

The term "database" as used herein, refers to any form of one or more (or combination of) relational databases, object-oriented databases, hierarchical databases, network databases, non-relational (e.g. NoSQL) databases, document store databases, in-memory databases, programs, tables, files, lists, or any form of programming structure or structures that function to store data as described herein.

The term "computer memory" as used herein refers to any tangible, non-transitory storage that participates in providing instructions to a processor for execution. Such a medium may take many forms, including but not limited to, non-volatile media, volatile media, and any equivalent media known in the art. Non-volatile media includes, for example, ROM, magnetic media, and optical storage media. Volatile media includes, for example, DRAM, which typically serves as main memory. Common forms of computer memory include, for example, hard drives and other forms of magnetic media, optical media such as CD-ROM disks, as well as various forms of RAM, ROM, PROM, EPROM, FLASH-EPROM, solid state media such as memory cards, and any other form of memory chip or cartridge, or any other medium from which a computer can read. While several examples are provided above, these examples are not meant to be limiting, but illustrative of several common examples, and any similar or equivalent devices or systems may be used that are known to those skilled in the art.

Various embodiments now will be described more fully hereinafter with reference to the accompanying drawings, which form a part hereof, and which show, by way of illustration, specific exemplary embodiments by which the innovations may be practiced. The embodiments may, however, be embodied in many different forms and should not be construed as limited to the embodiments set forth herein; rather, these embodiments are provided so that this disclosure will be thorough and complete, and will fully convey the scope of the embodiments to those skilled in the art. Among other things, the various embodiments may be methods, systems, media, devices, or any similar or equivalent arrangements known to those skilled in the art. Accordingly, the various embodiments may take the form of an entirely hardware embodiment, an entirely software embodiment or an embodiment combining software and hardware aspects. The following detailed description is, therefore, not to be taken in a limiting sense.

FIG. 1 is a block diagram of one embodiment of a computer system 20 having a germ alert program 30 that embodies the present invention. As shown in FIG. 1, the germ alert system 10 includes a computer device 22 comprising a computer processor 24, a computer memory 26, and a bus (not shown) that couples various system components including the computer processor 24 to the computer memory 26. For purposes of this application, as discussed below, any element mentioned in the singular also includes the plural, so it is to be understood that the term "computer processor" also includes multiple processors, and the term "computer memory" includes multiple memory devices, and either of which may be configured in any manner known in the art (i.e., in a single device, or distributed in any manner known to those skilled in the art).

As shown in FIG. 1, the computer memory 26 may include, operably installed thereupon, the germ alert program 30 and a database 28, each discussed further below. In various embodiments, the computer device 22 (or devices) may interact with a plurality of user devices 32, and a plurality of disinfection devices 34, as discussed in greater detail below.

The plurality of user devices 32 may be any form of personal computer device having a computer processor and a memory capable of interacting with the germ alert program, e.g., a server, a desktop computer, a laptop, a smart phone, smart watch, a tablet, or any form of electronic device capable of functioning as described herein. The system 10 is able to transmit alert notifications to the devices 32, as discussed in greater detail below.

In this embodiment, the plurality of disinfection devices 34 may include first disinfection devices 36 and second disinfection devices 38. However, while first and second disinfection devices 36 and 38 are illustrated, there may be a greater or fewer number of different types of devices, either in the same location or multiple locations. It is anticipated that potentially millions of a wide variety of such devices may be included in the system 10 as discussed in more detail below.

As illustrated in FIG. 1, in this embodiment, the germ alert program 30 of the computer device 22 communicates with the first and second disinfection devices 36 and 38, and with the plurality of user devices 32, via a network 23, in this case via the global computer network known as the Internet. While a global network is used in this embodiment, the network 23 may include any form of network known in the art for communicating information from one computer device to another. For example, any form of local area networks (LANs), wide area networks (WANs), direct connections, such as through a universal serial bus (USB) port, other forms of computer-readable media, or any combination thereof. On an interconnected set of LANs, including those based on differing architectures and protocols, a router may act as a link between LANs, enabling messages to be sent from one to another. In addition, communication links within LANs typically include twisted wire pair or coaxial cable, while communication links between networks may utilize analog telephone lines, full or fractional dedicated digital lines including T1, T2, T3, and T4, Integrated Services Digital Networks (ISDNs), Digital Subscriber Lines (DSLs), wireless links including satellite links, or other communications links known to those skilled in the art. The network may further include any form of wireless network, including cellular systems, WLAN, Wireless Router (WR) mesh, or the like. Access technologies such as 2G, 3G, 4G, and future access networks may enable wide area coverage for mobile devices. In essence, the wireless network may include any wireless communication mechanism known in the art by which information may travel between computers of the present system.

Figure 2:
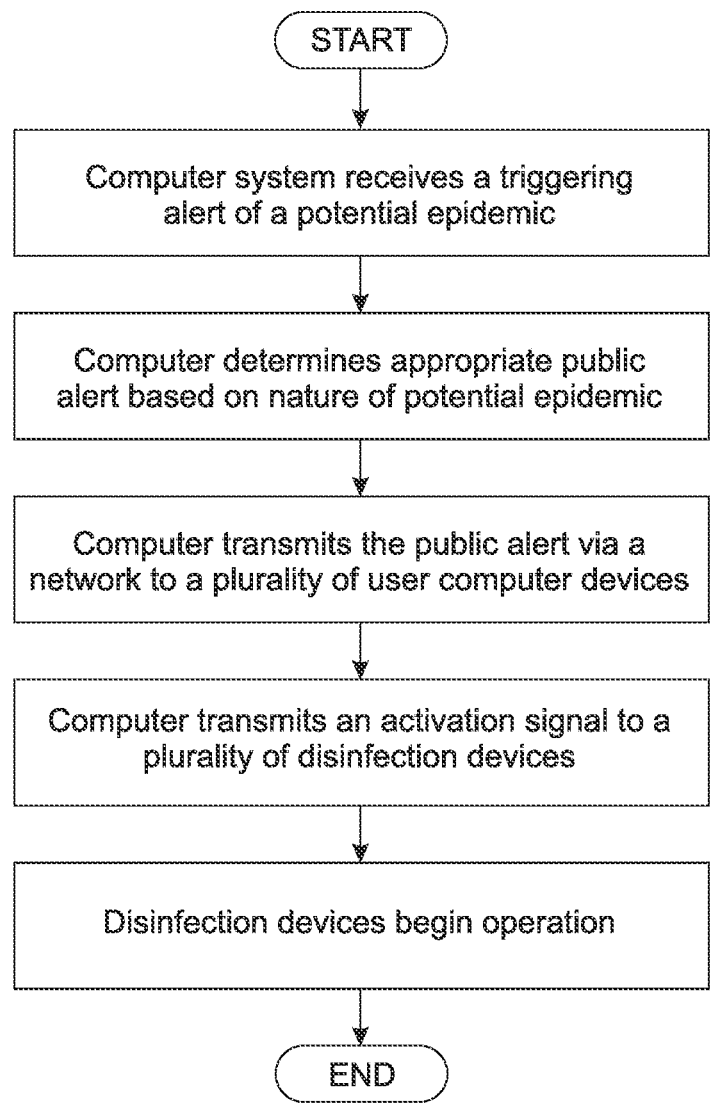
FIG. 2 a flow diagram of the operation of the computer system of FIG. 1.

FIG. 2 a flow diagram of the operation of the computer system 20 of FIG. 1. As illustrated in FIG. 1, the computer memory 26 of the computer device 22 includes the germ alert program 30, wherein the germ alert program 30 enables the computer system 20 to perform the process shown in FIG. 2. As shown in FIG. 2, the process includes the steps of first receiving a triggering alert of a potential epidemic. For purposes of this application, the term "epidemic" is defined to include any form of epidemic, pandemic, or other similar outbreak or emergency which requires mass warnings and triggering of a safety response.

In some embodiments, the germ alert program 30 includes a network of reporting agencies such as the WHO, the CDC, government medical staff, local hospitals and transport agencies, etc. The triggering alert may be sent from one or more of these reporting agencies, which may be in response to a variety of possible situations. For example, a triggering alert may be sent if a certain data threshold is reached within a determined area, such as number of elevated temperatures recorded at an airport, positive tests at one or more medical sites, etc., or longer term data that records viral transmission over time. Furthermore, the triggering alert may be sent any time there is a disease alert from any connected global source. Those skilled in the art administering the system 10 can determine a wide variety of events that may require activation of the system 10 to send an alert, and which persons or entities are authorized to make this determination and actually send the alert, and the geographical scope of the alert (e.g., a local area, a state, an entire nation, and/or other participating states or nations).

Some of this administrative apparatus already exists in the form of the Federal Emergency Management Agency (FEMA) and related agencies and offices which are authorized to use the existing Wireless Emergency Alerts (WEA) for sending a wide variety of alerts (including not only emergency situations, but also well-known AMBER alerts). These alerts may be sent not only to networks of smart phones and similar devices, but also via broadcast media, and these systems are anticipated to be incorporated and utilized by the present invention.

Once the computer 22 receives a triggering alert from the authorized person or agency, a public alert that is appropriate is determined. This may be automatically generated, or entered by administrative personnel may review the triggering alert and make a selection, or write a suitable alert. The public alert may be any form of an alert readily comprehensible to the public, e.g., a color coded system (yellow, red, etc.), a map showing danger areas, etc., and may include any relevant information, e.g., the name of a detected virus, procedures to take, additional instructions, etc. For example, persons in certain areas may be locked down at home, travel may be restricted, masks may be recommended or mandated, etc.

As shown in FIG. 2, the germ alert program 30 transmits the public alert via the network 23 to the plurality of user computer devices 32, and/or various broadcast media, as discussed above. The recipients of this alert may include all known persons in a given area or country, all persons who have opted in (or not opted out), or it may include only persons who have previously registered to receive such alerts.

The germ alert program 30 may also transmit an activation signal to the plurality of disinfection devices 34, causing the disinfection devices 34 to begin operation. As described above, the disinfection devices 34 may be placed in strategic locations determined to counter the spread of the potential epidemic, which may be any location which is known to accumulate germs, e.g., doorknobs, keypads, entryways, walkways, railings, common areas, baggage and baggage receptacles, etc., or any other areas or objects on which germs are easily spread. The disinfection devices 34 may already be positioned in the determined locations, or they may be moved or placed by personnel in response to the alert signal, wherein there may be a manual process for enabling or disabling the remote activation signal.

In order to best disinfect the given surface or location, various forms of disinfection devices 34 may be implemented. In some embodiments, the disinfection devices 34 may be various forms of UV radiation devices, e.g., a tablet, chamber, light strip, etc., one example being shown in FIG. 3 and discussed further below. Alternatively, the disinfection devices 34 may utilize other disinfecting means, e.g., a sanitizing spray, automatic wipe, heat radiation, ventilation, etc., or any other disinfecting means known to those skilled in the art.

Figure 3:
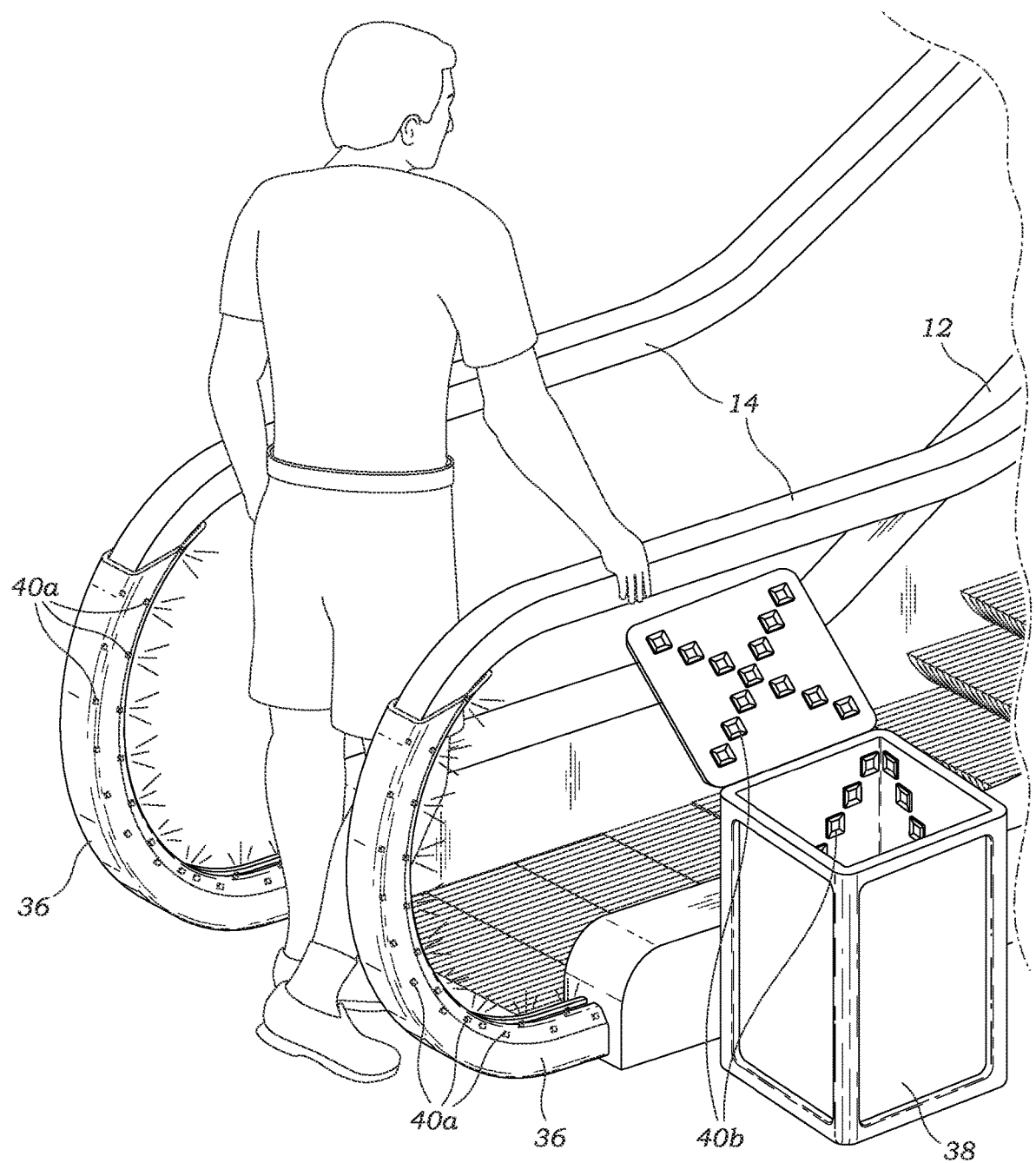
FIG. 3 illustrates one possible embodiment of a plurality of disinfection devices operating in public.

FIG. 3 illustrates one possible embodiment of the first plurality of disinfection devices 36 operating in public. Various disinfection devices may be located at strategic locations throughout a location with potential germ traffic, for example, an airport, train station, convention hall, event center, workplace, medical office, school, etc., or any other location deemed useful by relevant experts. As shown in FIG. 3, in this embodiment, the first disinfection devices 36 are shaped and adapted to be secured to hand rails 14 of any number of escalators 12. The first disinfection devices 36 are illustrated in the form of rail attachment members having UV lights 40a adapted to disinfect the escalator railing 14. The rail attachment members 36 may be removably attached or securely attached to the railing 14, and may be positioned on the lower end of the escalator 12 as illustrated, or on the upper end, or both. Obviously, the shape of the rail attachment members 36 may be adapted to any type of escalator rail, and in some embodiments may further be adapted for attachment to other types of railings such as retaining rails, stairs railing, etc.

As shown in FIG. 3, in this embodiment, the second disinfection devices 38 are in the form of a disinfecting chamber such as one adapted for disinfecting baggage passing through an area, wherein UV lights 40b are positioned within and/or upon the chamber 38 for disinfecting any items or baggage positioned within the chamber 38 for a period of time. In this embodiment, for example, all persons passing through a check point, such as at an airport or bus terminal, may pass through an area that is sanitized, and all bags, laptops, etc., may be placed in the chamber 38 for a period of time to ensure adequate disinfection.

As previously mentioned, the plurality of disinfecting devices 34 may in be different forms of devices than illustrated or described here, provided they are adapted to disinfect an item or area after the activation signal is received. For example, UV lights may be operably mounted to irradiate any desired location, e.g., elevator buttons, a computer keyboard, a door handle, a countertop, etc. The disinfecting devices 34 may also be any shape to conform to any desired item that may benefit from a disinfecting element. Furthermore, alternative disinfecting means may also be implemented (e.g., a spray, ventilator, heat radiation, other form of UV radiation, etc., or any other means).

Upon receiving the activation signal, e.g., via a wireless signal, each of the first and second disinfection devices 36 and 38 begin to operate to disinfect the area, until the germ alert program 30 instructs them to stop. In this embodiment, the UV lights 40 may turn on to disinfect the surrounding area of both the rail attachment members 36 and the disinfecting chamber 38. In some implementations, disinfection devices 34/36/38 may have a motion sensing feature (not shown), wherein the activation signal may cause operation of the motion sensing feature instead of the disinfecting feature, such that the disinfecting feature is triggered when motion is detected.

The title of the present application, and the claims presented, do not limit what may be claimed in the future, based upon and supported by the present application. Furthermore, any features shown in any of the drawings may be combined with any features from any other drawings to form an invention which may be claimed.

As used in this application, the words "a," "an," and "one" are defined to include one or more of the referenced item unless specifically stated otherwise. The terms "approximately" and "about" are defined to mean+/−10%, unless otherwise stated. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application. While the invention has been described with reference to at least one particular embodiment, it is to be clearly understood that the invention is not limited to these embodiments, but rather the scope of the invention is defined by claims made to the invention.

What is claimed is:

1. A method for alerting a public population of a potential epidemic and for responding automatically to try to prevent the potential epidemic, the method comprising the steps of:
   providing a plurality of disinfection devices;
   positioning the plurality of disinfection devices in strategic locations determined to counter the spread of the potential epidemic;
   providing a germ alert system comprising a computer device having a computer processor and a computer memory, the computer memory having a germ alert program operably installed thereupon;
   receiving by the germ alert system a triggering alert of the potential epidemic from one of a network of government health agencies comprising World Health Organization, Center for Disease Control, or an equivalent government body;
determining via the germ alert system a public alert based upon the nature of the potential epidemic;
transmitting to the public population via the germ alert system the public alert via a public emergency alert system, the public emergency alert system comprising the United States Wireless Emergency Alert system or an equivalent government alert system; and
transmitting via the germ alert system, automatically and concurrently with the transmittal of the public alert, an activation signal to the plurality of disinfection devices so that the plurality of disinfection devices begin operation to counter the potential epidemic.

2. The germ alert system of claim 1, wherein the plurality of disinfection devices are UV radiation devices.

3. The germ alert system of claim 2, wherein the UV radiation devices are positioned at airports.

4. The germ alert system of claim 3, wherein the UV radiation devices are positioned to irradiate luggage passing through the airport.

5. The germ alert system of claim 3, wherein the UV radiation devices are positioned at airports to irradiate elevator buttons within the airport.

6. The germ alert system of claim 3, wherein the UV radiation devices are positioned to irradiate counter tops at airports.

7. The germ alert system of claim 1, wherein the radiation devices are positioned to disinfect keypads.

8. The germ alert system of claim 1, wherein the radiation devices are positioned to disinfect doorknobs, or railings.

9. The germ alert system of claim 1, wherein the public alert includes a color coded system that alerts the public population of the severity of the potential epidemic.

10. The germ alert system of claim 1, wherein the public alert includes a map that shows the public population areas that are the most severely affected by the potential epidemic.

11. The germ alert system of claim 1, wherein the public alert includes instructions for the public population to follow to avoid or mitigate the potential epidemic.

* * * * *